United States Patent [19]
Vahlensieck et al.

[11] Patent Number: 5,641,666
[45] Date of Patent: Jun. 24, 1997

[54] SORAPHEN A RESISTANT FUNGI AND ACETYL-COA CARBOXYLASE

[75] Inventors: Hans-Friedrich Vahlensieck, Basel, Switzerland; Albert Hinnen, Jena, Germany

[73] Assignee: Novartis Corporation, Tarrytown, N.Y.

[21] Appl. No.: 354,973

[22] Filed: Dec. 13, 1994

[30] Foreign Application Priority Data

Dec. 17, 1993 [GB] United Kingdom ............... 9325819

[51] Int. Cl.$^6$ .................. C12N 9/00; C07H 21/04
[52] U.S. Cl. ........................... 435/183; 536/23.2
[58] Field of Search ................. 435/183, 69.1; 536/23.2

[56] References Cited

PUBLICATIONS

Al–Feel, W., et al., "Cloning of the Yeast FAS3 Gene and Primary Structure of Yeast Acetyl–CoA Carboxylase", *PNAS*, 89:4534–4538 (1992).

Klebe, R.J., et al., "A General Method for Polyethylene–glycol–induced Genetic Transformation of Bacteria and Yeast", *Gene*, 25:333–341 (1983).

Matsuhashi, M., "Acetyl–CoA Carboxylast from Yeast", *Methods in Enzymology*, Lowenstein, J.M., Ed., 14:3–8 (1969).

Sikorski, R.S., et al., "A System of Shuttle Vectors and Yeast Host Strains Designed for Efficient Manipulation of DNA in *Saccharomyces cerevisiae*", *Genetics*, 122:19–27 (1989).

Vahlensieck, H.–F., Ph.D. Thesis, "A Genetic Approach to Determine the Biochemical Target of the Antimicrobial Agent, Soraphen A", Philosophisch–Naturwissenschaftlichen Fakultät der Universität Basel (1993).

Vahlensieck, H.F. et al. (1994) "Identification of the yeast ACC1 gene product (acetyl–CoA carboxylase) as the target of the polyketide fungicide soraphen A" *Curr. Genet.* 25:95–100.

Roessler, P.G. (1993) "Genetic engineering approaches for enhanced production of biodiesel fuel from microalgae" *Abstr. Pap. Am. Chem. Soc.* 205 Meet., Pt. 2:BTEC29.

*Primary Examiner*—Robert A. Wax
*Assistant Examiner*—Kawai Lau
*Attorney, Agent, or Firm*—Gary M. Pace

[57] ABSTRACT

The present invention discloses DNA molecules comprising a gene encoding yeast acetyl-coenzyme A carboxylase resistant to soraphen A inhibition. Mutations confering soraphen A resistance to acetyl-CoA carboxylase can be dominant or recessive, and they can be point mutations, deletion or insertion mutations. In addition methods of isolating a gene encoding fungal acetyl-coenzyme A carboxylase resistant to soraphen A inhibition are provided as well as methods for purifying fungal acetyl-coenzyme A carboxylase resistant to soraphen A inhibition. Purified enzyme can be used in assays to identify inhibitors of soraphen A resistant acetyl-coenzyme A carboxylase.

3 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 2237 amino acids
    ( B ) TYPE: amino acid
    ( C ) STRANDEDNESS: single -continued (D) TOPOLOGY: linear (ii) MOLECULE TYPE: Protein (iii) HYPOTHETICAL: NO (xi) SEQUENCE DESCRIPTION: SEQ ID NO:1:

```
Met  Ser  Glu  Glu  Ser  Leu  Phe  Glu  Ser  Pro  Gln  Lys  Met  Glu  Tyr
1                 5                      10                       15
Glu  Ile  Thr  Asn  Tyr  Ser  Glu  Arg  His  Thr  Glu  Leu  Pro  Gly  His  Phe
              20                      25                       30
Ile  Gly  Leu  Asn  Thr  Val  Asp  Lys  Leu  Glu  Glu  Ser  Pro  Leu  Arg  Asp
              35                      40                       45
Phe  Val  Lys  Ser  His  Gly  Gly  His  Thr  Val  Ile  Ser  Lys  Ile  Leu  Ile
     50                      55                       60
Ala  Asn  Asn  Gly  Ile  Ala  Ala  Val  Lys  Glu  Ile  Arg  Ser  Val  Arg  Lys
65                           70                       75                       80
Trp  Ala  Tyr  Glu  Thr  Phe  Gly  Asp  Asp  Arg  Thr  Val  Gln  Phe  Val  Ala
                   85                      90                       95
Met  Ala  Thr  Pro  Glu  Asp  Leu  Glu  Ala  Asn  Ala  Glu  Tyr  Ile  Arg  Met
              100                     105                      110
Ala  Asp  Gln  Tyr  Ile  Glu  Val  Pro  Gly  Gly  Thr  Asn  Asn  Asn  Asn  Tyr
              115                     120                      125
Ala  Asn  Val  Asp  Leu  Ile  Val  Asp  Ile  Ala  Glu  Arg  Ala  Asp  Val  Asp
     130                     135                      140
Ala  Val  Trp  Ala  Gly  Trp  Gly  His  Ala  Ser  Glu  Asn  Pro  Leu  Leu  Pro
145                     150                      155                      160
Glu  Lys  Leu  Ser  Gln  Ser  Lys  Arg  Lys  Val  Ile  Phe  Ile  Gly  Pro  Pro
                   165                     170                      175
Gly  Asn  Ala  Met  Arg  Ser  Leu  Gly  Asp  Lys  Ile  Ser  Ser  Thr  Ile  Val
              180                     185                      190
Ala  Gln  Ser  Ala  Lys  Val  Pro  Cys  Ile  Pro  Trp  Ser  Gly  Thr  Gly  Val
     195                     200                      205
Asp  Thr  Val  His  Val  Asp  Glu  Lys  Thr  Gly  Leu  Val  Ser  Val  Asp  Asp
     210                     215                      220
Asp  Ile  Tyr  Gln  Lys  Gly  Cys  Cys  Thr  Ser  Pro  Glu  Asp  Gly  Leu  Gln
225                     230                      235                      240
Lys  Ala  Lys  Arg  Ile  Gly  Phe  Pro  Val  Met  Ile  Lys  Ala  Ser  Glu  Gly
                   245                     250                      255
Gly  Gly  Gly  Lys  Gly  Ile  Arg  Gln  Val  Glu  Arg  Glu  Glu  Asp  Phe  Ile
              260                     265                      270
Ala  Leu  Tyr  His  Gln  Ala  Ala  Asn  Glu  Ile  Pro  Gly  Ser  Pro  Ile  Phe
     275                     280                      285
Ile  Met  Lys  Leu  Ala  Gly  Arg  Ala  Arg  His  Leu  Glu  Val  Gln  Leu  Leu
     290                     295                      300
Ala  Asp  Gln  Tyr  Gly  Thr  Asn  Ile  Ser  Leu  Phe  Gly  Arg  Asp  Cys  Ser
305                     310                      315                      320
Val  Gln  Arg  Arg  His  Gln  Lys  Ile  Ile  Glu  Glu  Ala  Pro  Val  Thr  Ile
                   325                     330                      335
Ala  Lys  Ala  Glu  Thr  Phe  His  Glu  Met  Glu  Lys  Ala  Ala  Val  Arg  Leu
              340                     345                      350
Gly  Lys  Leu  Val  Gly  Tyr  Val  Ser  Ala  Gly  Thr  Val  Glu  Tyr  Leu  Tyr
     355                     360                      365
Ser  His  Asp  Asp  Gly  Lys  Phe  Tyr  Phe  Leu  Glu  Leu  Asn  Pro  Arg  Leu
     370                     375                      380
```

```
Gln  Val  Glu  His  Pro  Thr  Thr  Glu  Met  Val  Ser  Gly  Val  Asn  Leu  Pro
385                      390                 395                           400

Ala  Ala  Gln  Leu  Gln  Ile  Ala  Met  Gly  Ile  Pro  Met  His  Arg  Ile  Ser
                    405                 410                           415

Asp  Ile  Arg  Thr  Leu  Tyr  Gly  Met  Asn  Pro  His  Ser  Ala  Ser  Glu  Ile
               420                 425                      430

Asp  Phe  Glu  Phe  Lys  Thr  Gln  Asp  Ala  Thr  Lys  Lys  Gln  Arg  Arg  Pro
          435                 440                      445

Ile  Pro  Lys  Gly  His  Cys  Thr  Ala  Cys  Arg  Ile  Thr  Ser  Glu  Asp  Pro
     450                 455                      460

Asn  Asp  Gly  Phe  Lys  Pro  Ser  Gly  Gly  Thr  Leu  His  Glu  Leu  Asn  Phe
465                      470                 475                           480

Arg  Ser  Ser  Ser  Asn  Val  Trp  Gly  Tyr  Phe  Ser  Val  Gly  Asn  Asn  Gly
               485                 490                           495

Asn  Ile  His  Ser  Phe  Ser  Asp  Ser  Gln  Phe  Gly  His  Ile  Phe  Ala  Phe
               500                 505                      510

Gly  Glu  Asn  Arg  Gln  Ala  Ser  Arg  Lys  His  Met  Val  Val  Ala  Leu  Lys
               515                 520                      525

Glu  Leu  Ser  Ile  Arg  Gly  Asp  Phe  Arg  Thr  Thr  Val  Glu  Tyr  Leu  Ile
          530                 535                      540

Lys  Leu  Leu  Glu  Thr  Glu  Asp  Phe  Glu  Asp  Asn  Thr  Ile  Thr  Thr  Gly
545                      550                 555                           560

Trp  Leu  Asp  Asp  Leu  Ile  Thr  His  Lys  Met  Thr  Ala  Glu  Lys  Pro  Asp
               565                 570                      575

Pro  Thr  Leu  Ala  Val  Ile  Cys  Gly  Ala  Ala  Thr  Lys  Ala  Phe  Leu  Ala
               580                 585                      590

Ser  Glu  Glu  Ala  Arg  His  Lys  Tyr  Ile  Glu  Ser  Leu  Gln  Lys  Gly  Gln
          595                 600                      605

Val  Leu  Ser  Lys  Asp  Leu  Leu  Gln  Thr  Met  Phe  Pro  Val  Asp  Phe  Ile
     610                 615                      620

His  Glu  Gly  Lys  Arg  Tyr  Lys  Phe  Thr  Val  Ala  Lys  Ser  Gly  Asn  Asp
625                      630                 635                           640

Arg  Tyr  Thr  Leu  Phe  Ile  Asn  Gly  Ser  Lys  Cys  Asp  Ile  Ile  Leu  Arg
               645                 650                           655

Gln  Leu  Ser  Asp  Gly  Gly  Leu  Leu  Ile  Ala  Ile  Gly  Gly  Lys  Ser  His
               660                 665                      670

Thr  Ile  Tyr  Trp  Lys  Glu  Glu  Val  Ala  Ala  Thr  Arg  Leu  Ser  Val  Asp
               675                 680                      685

Ser  Met  Thr  Thr  Leu  Leu  Glu  Val  Glu  Asn  Asp  Pro  Thr  Gln  Leu  Arg
     690                 695                      700

Thr  Pro  Ser  Pro  Gly  Lys  Leu  Val  Lys  Phe  Leu  Val  Glu  Asn  Gly  Glu
705                      710                 715                           720

His  Ile  Ile  Lys  Gly  Gln  Pro  Tyr  Ala  Glu  Ile  Glu  Val  Met  Lys  Met
                    725                 730                           735

Gln  Met  Pro  Leu  Val  Ser  Gln  Glu  Asn  Gly  Ile  Val  Gln  Leu  Leu  Lys
               740                 745                      750

Gln  Pro  Gly  Ser  Thr  Ile  Val  Ala  Gly  Asp  Ile  Met  Ala  Ile  Met  Thr
          755                 760                      765

Leu  Asp  Asp  Pro  Ser  Lys  Val  Lys  His  Ala  Leu  Pro  Phe  Glu  Gly  Met
     770                 775                      780

Leu  Pro  Asp  Phe  Gly  Ser  Pro  Val  Ile  Glu  Gly  Thr  Lys  Pro  Ala  Tyr
785                 790                      795                           800

Lys  Phe  Lys  Ser  Leu  Val  Ser  Thr  Leu  Glu  Asn  Ile  Leu  Lys  Gly  Tyr
                    805                 810                           815
```

```
Asp Asn Gln Val Ile Met Asn Ala Ser Leu Gln Gln Leu Ile Glu Val
                820             825             830
Leu Arg Asn Pro Lys Leu Pro Tyr Ser Glu Trp Lys Leu His Ile Ser
            835             840             845
Ala Leu His Ser Arg Leu Pro Ala Lys Leu Asp Glu Gln Met Glu Glu
850             855             860
Leu Val Ala Arg Ser Leu Arg Arg Gly Ala Val Phe Pro Ala Arg Gln
865             870             875             880
Leu Ser Lys Leu Ile Asp Met Ala Val Lys Asn Pro Glu Tyr Asn Pro
                885             890             895
Asp Lys Leu Leu Gly Ala Val Glu Pro Leu Ala Asp Ile Ala His
                900             905             910
Lys Tyr Ser Asn Gly Leu Glu Ala His Glu His Ser Ile Phe Val His
            915             920             925
Phe Leu Glu Glu Tyr Tyr Glu Val Glu Lys Leu Phe Asn Gly Pro Asn
930             935             940
Val Arg Glu Glu Asn Ile Ile Leu Lys Leu Arg Asp Glu Asn Pro Lys
945             950             955             960
Asp Leu Asp Lys Val Ala Leu Thr Val Leu Ser His Ser Lys Val Ser
                965             970             975
Ala Lys Asn Asn Leu Ile Leu Ala Ile Leu Lys His Tyr Gln Pro Leu
            980             985             990
Cys Lys Leu Ser Ser Lys Val Ser Ala Ile Phe Ser Thr Pro Leu Gln
            995             1000            1005
His Ile Val Glu Leu Glu Ser Lys Ala Thr Ala Lys Val Ala Leu Gln
            1010            1015            1020
Ala Arg Glu Ile Leu Ile Gln Gly Ala Leu Pro Ser Val Lys Glu Arg
1025            1030            1035            1040
Thr Glu Gln Ile Glu His Ile Leu Lys Ser Ser Val Val Lys Val Ala
                1045            1050            1055
Tyr Gly Ser Ser Asn Pro Lys Arg Ser Glu Pro Asp Leu Asn Ile Leu
            1060            1065            1070
Lys Asp Leu Ile Asp Ser Asn Tyr Val Val Phe Asp Val Leu Leu Gln
            1075            1080            1085
Phe Leu Thr His Gln Asp Pro Val Val Thr Ala Ala Ala Ala Gln Val
            1090            1095            1100
Tyr Ile Arg Arg Ala Tyr Arg Ala Tyr Thr Ile Gly Asp Ile Arg Val
1105            1110            1115            1120
His Glu Gly Val Thr Val Pro Ile Val Glu Trp Lys Phe Gln Leu Pro
                1125            1130            1135
Ser Ala Ala Phe Ser Thr Phe Pro Thr Val Lys Ser Lys Met Gly Met
                1140            1145            1150
Asn Arg Ala Val Ser Val Ser Asp Leu Ser Tyr Val Ala Asn Ser Gln
            1155            1160            1165
Ser Ser Pro Leu Arg Glu Gly Ile Leu Met Ala Val Asp His Leu Asp
            1170            1175            1180
Asp Val Asp Glu Ile Leu Ser Gln Ser Leu Glu Val Ile Pro Arg His
1185            1190            1195            1200
Gln Ser Ser Ser Asn Gly Pro Ala Pro Asp Arg Ser Gly Ser Ser Ala
                1205            1210            1215
Ser Leu Ser Asn Val Ala Asn Val Cys Val Ala Ser Thr Glu Gly Phe
            1220            1225            1230
Glu Ser Glu Glu Glu Ile Leu Val Arg Leu Arg Glu Ile Leu Asp Leu
```

-continued

```
                 1235                    1240                     1245
  Asn  Lys  Gln  Glu  Leu  Ile  Asn  Ala  Ser  Ile  Arg  Arg  Ile  Thr  Phe  Met
            1250                    1255                    1260
  Phe  Gly  Phe  Lys  Asp  Gly  Ser  Tyr  Pro  Lys  Tyr  Tyr  Thr  Phe  Asn  Gly
  1265                1270                    1275                         1280
  Pro  Asn  Tyr  Asn  Glu  Asn  Glu  Thr  Ile  Arg  His  Ile  Glu  Pro  Ala  Leu
                 1285                    1290                    1295
  Ala  Phe  Gln  Leu  Glu  Leu  Gly  Arg  Leu  Ser  Asn  Phe  Asn  Ile  Lys  Pro
                 1300                    1305                    1310
  Ile  Phe  Thr  Asp  Asn  Arg  Asn  Ile  His  Val  Tyr  Glu  Ala  Val  Ser  Lys
                 1315                    1320                    1325
  Thr  Ser  Pro  Leu  Asp  Lys  Arg  Phe  Phe  Thr  Arg  Gly  Ile  Ile  Arg  Thr
                 1330                    1335                    1340
  Gly  His  Ile  Arg  Asp  Asp  Ile  Ser  Ile  Gln  Glu  Tyr  Leu  Thr  Ser  Glu
  1345                1350                    1355                         1360
  Ala  Asn  Arg  Leu  Met  Ser  Asp  Ile  Leu  Asp  Asn  Leu  Glu  Val  Thr  Asp
                 1365                    1370                    1375
  Thr  Ser  Asn  Ser  Asp  Leu  Asn  His  Ile  Phe  Ile  Asn  Phe  Ile  Ala  Val
                 1380                    1385                    1390
  Phe  Asp  Ile  Ser  Pro  Glu  Asp  Val  Glu  Ala  Ala  Phe  Gly  Gly  Phe  Leu
                 1395                    1400                    1405
  Glu  Arg  Phe  Gly  Lys  Arg  Leu  Leu  Arg  Leu  Arg  Val  Ser  Ser  Ala  Glu
                 1410                    1415                    1420
  Ile  Arg  Ile  Ile  Ile  Lys  Asp  Pro  Gln  Thr  Gly  Ala  Pro  Val  Pro  Leu
  1425                1430                    1435                         1440
  Arg  Ala  Leu  Ile  Asn  Asn  Val  Ser  Gly  Tyr  Val  Ile  Lys  Thr  Glu  Met
                 1445                    1450                    1455
  Tyr  Thr  Glu  Val  Lys  Asn  Ala  Lys  Gly  Glu  Trp  Val  Phe  Lys  Ser  Leu
                 1460                    1465                    1470
  Gly  Lys  Pro  Gly  Ser  Met  His  Leu  Arg  Pro  Ile  Ala  Thr  Pro  Tyr  Pro
                 1475                    1480                    1485
  Val  Lys  Glu  Trp  Leu  Gln  Pro  Lys  Arg  Tyr  Lys  Ala  His  Leu  Met  Gly
                 1490                    1495                    1500
  Thr  Thr  Tyr  Val  Tyr  Asp  Phe  Pro  Glu  Leu  Phe  Arg  Gln  Ala  Ser  Ser
  1505                1510                    1515                         1520
  Ser  Gln  Gly  Lys  Asn  Phe  Ser  Ala  Asp  Val  Lys  Leu  Thr  Asp  Asp  Phe
                 1525                    1530                    1535
  Phe  Ile  Ser  Asn  Glu  Leu  Ile  Glu  Asp  Glu  Asn  Gly  Glu  Leu  Thr  Glu
                 1540                    1545                    1550
  Val  Glu  Arg  Glu  Pro  Gly  Ala  Asn  Ala  Ile  Gly  Met  Val  Ala  Phe  Lys
                 1555                    1560                    1565
  Ile  Thr  Val  Lys  Thr  Pro  Glu  Tyr  Pro  Arg  Gly  Arg  Gln  Phe  Val  Val
  1570                1575                    1580
  Val  Ala  Asn  Asp  Ile  Thr  Phe  Lys  Ile  Gly  Ser  Phe  Gly  Pro  Gln  Glu
  1585                1590                    1595                         1600
  Asp  Glu  Phe  Phe  Asn  Lys  Val  Thr  Glu  Tyr  Ala  Arg  Lys  Arg  Gly  Ile
                 1605                    1610                    1615
  Pro  Arg  Ile  Tyr  Leu  Ala  Ala  Asn  Ser  Gly  Ala  Arg  Ile  Gly  Met  Ala
                 1620                    1625                    1630
  Glu  Glu  Ile  Val  Pro  Leu  Phe  Gln  Val  Ala  Trp  Asn  Asp  Ala  Ala  Asn
                 1635                    1640                    1645
  Pro  Asp  Lys  Gly  Phe  Gln  Tyr  Leu  Tyr  Leu  Thr  Ser  Glu  Gly  Met  Glu
                 1650                    1655                    1660
```

```
Thr Leu Lys Lys Phe Asp Lys Glu Asn Ser Val Leu Thr Glu Arg Thr
1665                1670                1675                1680

Val Ile Asn Gly Glu Glu Arg Phe Val Ile Lys Thr Ile Ile Gly Ser
                1685                1690                1695

Glu Asp Gly Leu Gly Val Glu Cys Leu Arg Gly Ser Gly Leu Ile Ala
                1700                1705                1710

Gly Ala Thr Ser Arg Ala Tyr His Asp Ile Phe Thr Ile Thr Leu Val
                1715                1720                1725

Thr Cys Arg Ser Val Gly Ile Gly Ala Tyr Leu Val Arg Leu Gly Gln
                1730                1735                1740

Arg Ala Ile Gln Val Glu Gly Gln Pro Ile Ile Trp Tyr Arg Cys Leu
1745                1750                1755                1760

Leu Thr Gly Ala Pro Glu Ser Thr Asn Ala Gly Arg Glu Val Tyr Thr
                1765                1770                1775

Ser Asn Leu Gln Leu Gly Gly Thr Gln Ile Met Tyr Asn Asn Gly Val
                1780                1785                1790

Ser His Leu Thr Ala Val Asp Asp Leu Ala Gly Val Glu Lys Ile Val
                1795                1800                1805

Glu Trp Met Ser Tyr Val Pro Ala Lys Arg Asn Met Pro Val Pro Ile
                1810                1815                1820

Leu Glu Thr Lys Asp Thr Trp Asp Arg Pro Val Asp Phe Thr Pro Thr
1825                1830                1835                1840

Asn Asp Glu Thr Tyr Asp Val Arg Trp Met Ile Glu Gly Arg Glu Thr
                1845                1850                1855

Glu Ser Gly Phe Glu Tyr Gly Leu Phe Asp Lys Gly Ser Phe Phe Glu
                1860                1865                1870

Thr Leu Ser Gly Trp Ala Lys Gly Val Val Val Gly Arg Ala Arg Leu
                1875                1880                1885

Gly Gly Ile Pro Leu Gly Val Ile Gly Val Glu Thr Arg Thr Val Glu
                1890                1895                1900

Asn Leu Ile Pro Ala Asp Pro Ala Asn Pro Asn Ser Ala Glu Thr Leu
1905                1910                1915                1920

Ile Gln Glu Pro Gly Gln Val Trp His Pro Asn Ser Ala Phe Lys Thr
                1925                1930                1935

Ala Gln Ala Ile Asn Asp Phe Asn Asn Gly Glu Gln Leu Pro Met Met
                1940                1945                1950

Ile Leu Ala Asn Trp Arg Gly Phe Ser Gly Gly Gln Arg Asp Met Phe
                1955                1960                1965

Asn Glu Val Leu Lys Tyr Gly Ser Phe Ile Val Asp Ala Leu Val Asp
                1970                1975                1980

Tyr Lys Gln Pro Ile Ile Ile Tyr Ile Pro Pro Thr Gly Glu Leu Arg
1985                1990                1995                2000

Gly Gly Ser Trp Val Val Val Asp Pro Thr Ile Asn Ala Asp Gln Met
                2005                2010                2015

Glu Met Tyr Ala Asp Val Asn Ala Arg Ala Gly Val Leu Glu Pro Gln
                2020                2025                2030

Gly Met Val Gly Ile Lys Phe Arg Arg Glu Lys Leu Leu Asp Thr Met
                2035                2040                2045

Asn Arg Leu Asp Asp Lys Tyr Arg Glu Leu Arg Ser Gln Leu Ser Asn
                2050                2055                2060

Lys Ser Leu Ala Pro Glu Val His Gln Gln Ile Ser Lys Gln Leu Ala
2065                2070                2075                2080

Asp Arg Glu Arg Glu Leu Leu Pro Ile Tyr Gly Gln Ile Ser Leu Gln
                2085                2090                2095
```

| | | | | | | | | | | | | | | |
|---|---|---|---|---|---|---|---|---|---|---|---|---|---|---|
|Phe|Ala|Asp|Leu|His|Asp|Arg|Ser|Ser|Arg|Met|Val|Ala|Lys|Gly|Val
| | | |2100| | | |2105| | | | |2110| | |
|Ile|Ser|Lys|Glu|Leu|Glu|Trp|Thr|Glu|Ala|Arg|Arg|Phe|Phe|Phe|Trp
| | |2115| | | |2120| | | | |2125| | | |
|Arg|Leu|Arg|Arg|Arg|Leu|Asn|Glu|Glu|Tyr|Leu|Ile|Lys|Arg|Leu|Ser
| |2130| | | |2135| | | | |2140| | | | |
|His|Gln|Val|Gly|Glu|Ala|Ser|Arg|Leu|Glu|Lys|Ile|Ala|Arg|Ile|Arg
|2145| | | |2150| | | | |2155| | | | |2160|
|Ser|Trp|Tyr|Pro|Ala|Ser|Val|Asp|His|Glu|Asp|Asp|Arg|Gln|Val|Ala
| | | |2165| | | |2170| | | | |2175| | |
|Thr|Trp|Ile|Glu|Glu|Asn|Tyr|Lys|Thr|Leu|Asp|Asp|Lys|Leu|Lys|Gly
| | |2180| | | |2185| | | | |2190| | | |
|Leu|Lys|Leu|Glu|Ser|Phe|Ala|Gln|Asp|Leu|Ala|Lys|Lys|Ile|Arg|Ser
| |2195| | | |2200| | | | |2205| | | | |
|Asp|His|Asp|Asn|Ala|Ile|Asp|Gly|Leu|Ser|Glu|Val|Ile|Lys|Met|Leu
|2210| | | |2215| | | | |2220| | | | | |
|Ser|Thr|Asp|Asp|Lys|Glu|Lys|Leu|Leu|Lys|Thr|Leu|Lys| | | |
|2225| | | |2230| | | | |2235| | | | | | |

SORAPHEN A RESISTANT FUNGI AND ACETYL-COA CARBOXYLASE

The present invention relates to genes encoding an acetyl-coenzyme A carboxylase resistant to soraphen A inhibition, methods of isolating these genes, purified acetylcoenzyme A carboxylase resistant to soraphen A inhibition and assays to identify inhibitors of soraphen A resistant acetyl-coenzyme A (acetyl-CoA) carboxylase.

The 18-membered macrolide soraphen A, is a secondary metabolite of the myxobacterium *Sorangium cellulosum*, strain So ce 26. The chemical structure of Soraphen A is shown in formula (I).

Until now over 60 natural variants of soraphen A could be isolated (Augustiniak et at, 'Chemische Arbeiten', in: 'Wissenschafdicher Ergebnisbericht', Seiten 36–40, GBF Braunschweig, 1989). Soraphen A exhibits strong activity as a fungicide, while it is without effect on bacteria. In one instance it was shown to interfere with acetyl-CoA carboxylase (Pridzun, 'Untersuchungen zum Wirkungsmechanismus yon Soraphen A', Technische Universität Braunschweig, Germany, doctoral thesis) which is a key enzyme in fatty acid biosynthesis.

The main objective of the present invention is to provide soraphen A resistant genes which genes are able to confer soraphen A resistance to a host organism comprising said genes. It has now surprisingly been found that all soraphen A resistant genes so far isolated in yeast, a model system for fungi, are mutated in a single gene. The gene is identified to be yeast acetyl-CoA carboxylase the DNA sequence of which is known (Al-Feel et al, Proc. Nail. Acad. Sci. USA 89:4534–4538, 1992). Thus yeast strains resistant to soraphen A surprisingly result from mutation of a single gene, namely acetyl-CoA carboxylase. The mutations show dominant, semidominant, or recessive phenotypes in heterozygous diploid strains.

The mutant genes according to the invention can be used to produce recombinant soraphen A resistant acetyl-CoA carboxylase, which in turn can be used in in vitro assays to determine the inhibitory effect of soraphen A derivatives or other compounds on the activity of the mutant acetyl-CoA carboxylase. These assays allow the identification of improved soraphen A derivatives which induce less fungi resistent to soraphen A or compounds which are useful in anti-resistance strategies.

The present invention relates primarily to a DNA molecule comprising a gene encoding acetyl-CoA carboxylase resistant to soraphen A inhibition, but especially to a molecule comprising a gene encoding fungal, preferably yeast acetyl-CoA carboxylase.

Acetyl-CoA carboxylase catalyzes the committed step in fatty acid biosynthesis, yielding malonyl-CoA, the donor of the two-carbon units for the synthesis of long-chain fatty acids. In higher and lower eucaryotes the enzyme is a multifunctional polypeptide forming tetramers comprising domains for biotin binding, biotin carboxylation, and transcarboxylation. The yeast, chicken and rat carboxylases have an overall sequence identity of 34%.

Yeast acetyl-CoA carboxylase has a calculated molecular weight of about 250 kD and consists of about 2200 amino acids. The nucleotide sequence of the gene was determined by Al-Feel et at, Proc. Natl. Acad. Sci. USA 89:4534–4538, 1992. The biotin binding site and the biotin carboxylase domains are comprised by the N-terminal half of the yeast protein whereas the transcarboxylase domain is comprised by the C-terminal half. It has now been found that mutations confering soraphen A resistance are preferably located in the N-terminal half of the yeast acetyl-CoA carboxylase. Within the N-terminal half mutations and preferably dominant mutations in the biotin carboxylase domain are preferred which are assumed to block the enzymes ability to carboxylate biotin. The present invention thus primarily relates to genes encoding acetyl-CoA carboxylase resistant to soraphen A inhibition which comprise a mutation of the gene, and especially a mutation in the biotin carboxylase domain. Alternatively, mutations are preferred which inhibit tetramer formation.

Mutations confering soraphen A resistance to acetyl-CoA carboxylase and preferably to yeast acetyl-CoA carboxylase can be dominant or recessive, and they can be single or multiple point mutations, deletion or insertion mutations. Preferably the mutations are point mutations altering a codon which encodes an amino acid selected from the group consisting of unpolar (glycine, alanine, valine, leucine, isoleucine, phenylalanine, profine), polar (serine, threonine, cytosine, methionine, tryptophan, tyrosine, asparagine, glutamine), basic (lysine, arginine, Histidine), and acidic amirto acids (aspartic acid, glutamic acid). Codons which are preferred targets of mutation are codons which encode an amino acid selected from the group consisting of valine, serine, threonine, histidine, and lysine. Among the codons for polar amino acids, mutations are preferred which inhibit phosphorylation or dephosphorylation of the protein.

In a preferred embodiment of the invention the mutation is selected from the group consisting of mutations changing valine at amino acid position 50 to phenylalanine, histidine at amino acid position 53 to arginine, lysine at amino acid position 73 to arginine, and serine at amino acid position 77 to tyrosine. Most preferred is the mutation changing serine at amino acid position 77 to tyrosine (see SEQ ID NO:1).

Another object of the present invention is to provide methods of isolating a gene encoding fungal acetyl-CoA carboxylase resistant to soraphen A inhibition. In one embodiment of the invention the method comprises (a) selecting and isolating a fungal strain, and preferably a yeast strain, resistant to soraphen A;
(b) purifying restriction fragments of eDNA or genomic DNA of said resistant strain;
(c) cloning the restriction fragments in bacteria;
(d) probing the clones for the presence of restriction fragments obtainable from the gene encoding wild-type acetyl-coenzyme A carboxylase;
(e) isolating and sequencing the gene encoding soraphen A resistant acetyl-CoA carboxylase; and
(f) identifying the mutation or the mutations.

To select for example soraphen A resistant yeast strains, within a preferred embodiment of the invention $10^4$ to $10^{10}$ and preferably $10^6$ to $10^9$ yeast cells are plated on a solidified medium containing 0,1 to 50 µg/ml and preferably 1 to 10 µg/ml soraphen A. Mating of the resulting yeast swains, zygote isolation, sporulation and tetrad analysis can be performed as described by Guthrie and Fink, 'Guide to Yeast Genetics and Molecular Biology' in: 'Methods of Enzymology', volume 194, 1991. Spore viability from crosses involving acetyl-CoA carboxylase mutants can be increased by feeding the spores with a drop of YPD-FA. After further cultivation mutant strains are used to purify restriction fragments of eDNA or genomic DNA which result from complete or partial restriction digestion. The preparation of genomic DNA or of RNA from yeast and the synthesis of eDNA from the RNA constitute techniques well known in yeast gene technology. Restriction digestion of DNA is done according to the manufacturers'instructions supplied with the restriction enzymes. Preferably the restriction fragments result from restriction digestion using restriction enzymes which are known not to cut within the gene encoding wildtype acetyl-CoA carboxylase such as for example SacI. The purified restriction fragments are then spliced into known selectable DNA vector molecules and the resultant plasmids are used to transform bacteria such as *E. coli*, Bacillus or Streptomyces. Clonal colonies derived after transformation and selection with antibiotics such as neomycin, ampicillin, kanamycin or terramycin are probed by colony hybridization for restriction fragments obtainable from genes encoding wild-type acetyl-CoA carboxylase. Techniques for probing bacterial colonies are described in detail in Sambrook et al, Molecular Cloning: A Laboratory Manual, Cold Spring Harbor Laboratory Press, Cold Spring Harbor, N.Y., 1989, the relevant pans of which are herein incorporated by reference. Bacterial clones harbouring such DNA molecules are isolated, their plasmid DNA is prepared and the gene encoding soraphen A resistant acetyl-CoA carboxylase is sequenced. Optionally the isolated DNA molecules can be transformed into yeast before sequencing to test whether they are able to confer soraphen A resistance. The sequence obtained is compared to the sequence of the wild-type gene and mutations are identified. To avoid sequencing of the complete gene to identify the mutation confering soraphen A resistance, it is also possible to shuffle restriction fragments between the wild-type and the mutant genes using techniques of recombinant DNA known in the art. The chimaeric genes can be tested whether they are able to confer soraphen A resistance or not by transformation in yeast. This narrow down the DNA region responsible for resistance.

The methods exemplified above for yeast can accordingly be applied to alternative fungi, from which strains resistant to soraphen A inhibition can be isolated.

The soraphen A resistant genes obtained by this method can be dominant, semidominant, or recessive.

A different method of isolating a gene encoding fungal acetyl-CoA carboxylase resistant to soraphen A inhibition, comprises
(a) selecting and isolating a fungal strain, and preferably a yeast strain, resistant to soraphen A;
(b) purifying restriction fragments of cDNA or genomic DNA of said resistant strain;
(c) cloning the restriction fragments in the fungus by complementation;
(d) isolating soraphen A resistant transformants;
(e) isolating and sequencing the gene encoding soraphen A resistant acetyl-CoA carboxylase; and
(f) identifying the mutation or the mutations.

To clone a restriction fragment in a fungus but especially in yeast by complementation the restriction fragment either comprises the whole gene encoding acetyl-CoA carboxylase including promoter and termination signals, or the known wild-type sequence of the acetyl-CoA carboxylase gene is used to select a specific restriction fragment of the gene which allows splicing of the fragment inbetween promoter and termination sequences active in the fungus, but especially in yeast. The purified restriction fragments are spliced into known DNA vector molecules which preferably contain a marker gene selectible in yeast and the resultant plasmids are used to transform strains with a defective acetyl-CoA carboxylase. These strains are auxotrophic for fatty acids and can be grown in media supplemented with fatty acids. Preferably, media are supplemented with 0,005% to 1% and more preferably with 0,01% to 0,1% palmitic acid. Strains which have been transformed with a gene encoding acetyl-CoA carboxylase resistant to soraphen A are no longer more auxotrophic for fatty acids and can be grown on medium which is not supplemented with for example palmitic acid. Optionally they can be identified by expression of a marker gene selectible in yeast. The soraphen A resistant genes obtained by this method can be dominant, semidominant, or recessive. Preferably the method is used to obtain dominant alleles.

Yet another method of isolating a gene encoding fungal acetyl-CoA carboxylase resistant to soraphen A inhibition, comprises
(a) selecting and isolating a fungal strain, and preferably a yeast strain, resistant to soraphen A;
(b) preparing cDNA or genomic DNA from the resistant strain;
(c) using said DNA as template for polymerase chain reaction amplification with primers complementary to sequences of the wild-type acetyl-CoA carboxylase gene;
(d) isolating and sequencing the amplification products; and
(e) identifying the mutation or the mutations.

Polymerase chain reaction amplification can be done as described in Saiki et al, Science 239:487–491, 1988. In this in vitro process them are used chemically synthesised oligonucleotides of 10 bp to 40 bp, and preferably of 20 bp to 30 bp length complementary to sequences of the wild-type acetyl-CoA carboxylase gene, which are designed to make up the ends of the DNA sequence to be amplified. Under suitable conditions, hybridization of the oligonucleotides with the complementary regions on the target DNA single strands produced by denaturing occurs. The double-stranded regions produced in this manner are used as primers for the subsequent polymerase reaction and the process steps of denaturation, hybridization of the oligonucleotides and synthesis of DNA are repeated 15 to 40 and preferably 20 to 30 times. In this process there may be used in addition to DNA polymerases from *E. coil* especially heat-stable polymerases from thermophilic bacteria, for example *Thermus aquaticus*.

Amplification products are identified after gel electrophoresis and can be sequenced either directly or after splicing into DNA vector molecules and cloning in microorganisms such as *E. coli*. Normally the mutated acetyl-CoA carboxylase is not amplified as a single fragment but as several overlapping fragments. Therefore, the method can also be used to selectively isolate acetyl-CoA carboxylase gene sequences supposed to be mutated in soraphen A resistant genes.

The present invention also relates to a purified fungal acetyl-CoA carboxylase, but especially to a purified yeast acetyl-CoA carboxylase resistant to soraphen A inhibition and to a method of purifying said acetyl-CoA carboxylase resistant to soraphen A inhibition, comprising
(a) homogenization of fungal cells; and
(b) avidin affinity chromatography of protein.

For protein purification fungal cells are harvested by centrifugation and subsequently homogenized in a suitable buffer containing protease inhibitors. It is preferable to remove cell debris by centrifugation and/or ultracentrifugation and to precipitate protein using for example ammoniumsulfate. Ultimately protein is applied on an avidin-agarose gel column and eluted. The fractions giving the highest extinctions at 280 nm are pooled. For storing the purified protein it is possible to precipitate the combined fractions for example by ammonium sulfate and to redissolve the protein in buffer containing glycerol which can then be stored −70° C.

Once having identified and isolated genes encoding soraphen A resistant acetyl-CoA carboxylase a purified protein can be obtained from transgenic heterologous expression of said DNA, i.e., placing a recombinant DNA comprising a DNA sequence coding for a protein exhibiting acetyl-CoA carboxylase activity into an appropriate bacterial, yeast or other cell expression system. A method of producing purified recombinant fungal acetyl-CoA carboxylase resistant to soraphen A, comprises the steps of (a) transforming a host organism with recombinant DNA encoding soraphen A resistant fungal acetyl-CoA carboxylase; and (b) isolating the protein from the host organism or its culture supernatant.

Suitable hosts include bacteria such as *E. coil* and Bacillus. Other suitable expression system hosts include insect cells grown in culture. These insect cells may be infected with a baculovirus containing a recombinant DNA molecule according to the invention.

Alternatively, the baculovirus may be used to infect a living insect, and the insect cells used as an expression system host. The expression system host is then allowed to produce an expression supernatant. This allows facile generation of large mounts of purified recombinant acetyl-CoA carboxylase by isolating the enzyme from the expression supernatant.

Purified acetyl-CoA carboxylase can then be used in an assay to identify inhibitors of soraphen A resistant acetyl-CoA carboxylase, comprising (a) incubating a first sample of soraphen A resistant acetyl-CoA carboxylase and its substrate;

(b) measuring the reactivity of the acetyl-CoA carboxylase in step (a);

(c) incubating a second sample of soraphen A resistant acetyl-CoA carboxylase and its substrate in the presence of a sample comprising a compound suspected to inhibit the enzyme's reactivity;

(d) measuring the reactivity of the acetyl-CoA carboxylase in step (c); and (e) comparing the reactivities of acetyl-CoA carboxylase in steps (a) and (c).

Suitable acetyl-CoA carboxylase for the above assay can be obtained using the purification methods of the present invention. Suitable substrates are acetyl-CoA or structural analogs that are capable of being carboxylated by the enzyme and $HCO_3^-$ with the preferred substrate being acetyl-CoA and $NaHCO_3$. Preferably acetyl-CoA is at a concentration of about 0.1 mM to 10 mM, more preferably at at about 0.1 mM to 1 mM, and most preferably at about 0.5 mM.

In addition to the acetyl-CoA carboxylase and a suitable substrate, the reaction mixture can contain a suitable buffer, suitable cofactors and suitable divalent cations as cofactors. A suitable buffer includes any suitable biological buffer that can provide buffering capability at a pH conductive to the reaction requirements of the enzyme. Preferably the buffer provides buffering capability in the pH range 7 to 9, more preferably in the pH range 7.5 to 8.5, and most preferably at a pH of about 8.0, e.g. 50 mM Tris-HCl at pH 8.0. A preferred cofactor for acetyl-CoA carboxylase is ATP, preferably at a concentration of about 0.5 nM to about 100 nM, more preferably at about 3.75 nM. Preferably the divalent cation is a divalent metal cation, more preferably magnesium. Additional components of the reaction mixture can be for example BSA and EDTA. The reaction is carded out at a suitable temperature to allow the reaction to proceed. Such a suitable temperature is about 4° C. to about 40° C., more preferably from about room temperature to about 35° C., and most preferably at about 30° C. The most preferred reaction mixture contains 50 mM Tris-HCl pH 8.0, 10 mM $MgCl_2$, 7.5 g/l BSA, 3.75 nM ATP, 10 mM EDTA, $^{14}C$-labeled $NaHCO_3$ (10 µCi per sample with a specific activity of 52.4 µCi/µmol) and different amounts of acetyl-CoA carboxylase. Preferably the reaction is started with the addition of acetyl-CoA.

Uninhibited reactivity of the acetyl-CoA carboxylase is any measure of enzymatic activity of acetyl-CoA carboxylase while in the presence of suitable substrate only. Measures of enzymatic activity are generally know to those of skill in the art, including equilibrium constants, reaction velocities of the appearance of reaction products or the consumption of reaction substrates, reaction kinetics, thermodynamics of the reaction, spectrophotometric analysis of reaction products, detection of labeled reaction components, etc. See, generally, Segel, 'Biochemical Calculations', 2nd edition, John Wiley and Sons, New York (1976); Suelter, 'A Practigal Guide to Enzymology', John Wiley and Sons, New York (1985). The preferred method of measuring the enzymatic activity is to determine the amount of incorporated $^{14}C$ from $^{14}C$-labeled $NaHCO_3$ by scintillation.

Suitable inhibitor compounds are identified using the above methods. Inhibited reactivity is determined in the same manner as uninhibited reactivity but with the addition of an inhibitor of acetyl-CoA carboxylase. The concentration of the inhibitor may vary depending on the inhibitory activity, but generally it will be in an amount ranging from about 10 nM to about 200 mM, more preferably about 0.1 mM to about 100 mM, and most preferably about 1 mM to about 10 mM. Generally, the acetyl-CoA or other substrate will be added to a mixture containing the enzyme and inhibitor and then an enzyme activity will be determined as described previously.

Comparing the inhibited reactivity to the uninhibited reactivity of the acetyl-CoA carboxylase includes determining whether a significant decrease in enzyme activity is observed in the inhibited reactivity compared to the uninhibited reactivity. A significant decrease is a decrease in enzymatic activity that is larger than the margin of error inherent in the measurement technique, preferably a decrease by about 50% of the activity in the absence of the inhibitor, more preferably a decrease by about 90%, and most preferably a decrease to a level of enzymatic activity that is essentially undetectable.

Another assay to identify inhibitors of soraphen A resistant fungal acetyl-CoA carboxylase comprises (a) growing a first culture of a fungus resistant to soraphen A and recording the growth curve;

(b) growing a second culture of the fungus resistant to soraphen A in the presence of a sample comprising a compound suspected to inhibit the reactivity of soraphen A resistant acetyl-CoA carboxylase and recording the growth curve; and (c) comparing the growth curves recorded in steps (a) and (b).

To record the growth curve of a culture of for example yeast the culture medium is inoculated at a concentration of $10^4$ to $10^8$ and preferably 106 to 107 yeast cells per litre. Then the culture is grown at a temperature between 20° C. and 40° C., preferably at about 30° C. under continuous agitation. At intervals samples are withdrawn and their optical density is determined. Preferably the optical density is measured at 600 nm (OD600). The values of the OD600 correlate with cell density and are plotted against time measured from the starting point of the culture. Alternatively, aliquots of the culture are removed and the cell number is determined by counting under the microscope. The growth curves recorded in the presence of a compound suspected to inhibit acetyl-CoA carboxylase are compared to the growth curves recorded in the absence of an inhibitory compound. The compound is considered to exert a significant inhibitory effect if the slope of the growth curve of the inhibited culture is reduced by more than 50%, preferably more than 80% and most preferably more than 95% compared to the uninhibited culture.

The invention will be further described by reference to the following examples. These examples are provided for purposes of illustration only, and are not intended to be limiting unless otherwise specified.

EXAMPLES

Example 1

Media and strains
1.1. Media

The basic culture medium is YPD containing 1% Bacto-yeast extract (Bifco), 2% Bacto-peptone (Difco) and 2% glucose (Merck).

YPD-SOR-10 is YPD medium supplemented with 10 µg/ml soraphen A.

YPD-FA is YPD supplemented with fatty acid (0,03% palmitic acid, Fluka) and 1% Tween 40 (Fluka).

The synthetic minimal medium SDHL contains 0,67% yeast Nitrogen Base without amino acids (Difco), amino acids as required, and 2% glucose. SDHLS medium is used for yeast transformations by electroporation and is SDHL supplemented with 1M sorbitol.

For plates the media are solidified with 2% Bacto-Agar (Difco).
1.2. Strains

*Saccharomyces cerevisiae* strain YS 18 (MATeα; his 3–11, 3–15; leu 2–3, 2–112; ura 3–Δ5; can$^R$; cir$^+$) is chosen as the wild-type. YHV 18 (MATa; his 3–11, 3–15; leu 2–3, 2–112; ura 3–Δ5; canst; cir$^+$) is isolated after a mating type switch of YS 18 and is therefore isogenic.

Example 2

Mating-type switch

YS 18 is transformed with plasmid pGAL-HO, containing the gene for the mating-type sequence-specific endonuclease HO under the control of the GAL promoter and the URA3 marker gene, according to the method of Klebe (Klebe et al, Gene 52:333–341, 1983). pGAL-HO was kindly provided by Dr. P. Lindner, Biocenter, Basel, Switzerland. The HO gene is switched on by growing the transformants for 2 hours on complete medium containing 2% galactose instead of glucose. The culture is plated on YPD plates and screened for "a" mating type colonies using an appropriate 'α' tester strain. Next the pGAL-HO plasmid is aborted using 5-fluoro-orotic acid (Pharmacia). Plasmid loss is confirmed by Southern analysis or PCR. After crosses with tester strains, about 80% of the cells sporulate after 3 days; spore viability is greater than 95%.

Example 3

Isolation of mutants

Each of the isogenic strains YS 18 and YHV 18 is grown in 5 ml of YPD to late exponential phase. The culture is diluted $10^4$ fold to give culture A the viable cell number of which is determined. Twenty tubes each containing 5 ml of YPD are inoculated with 10 µl of culture A, which corresponds to about 10 cells, and are incubated at 28° C. until a density of $10^7$ cells/ml is attained. 1 ml aliquots of each of the tubes are plated on YPD-SOR-10 and the plates are incubated at 30° C. for 3 days. To ensure isolation of independent mutants from each of the 20 YPD-SOR-10 plates only colonies with different shape or sizes are selected. Mutant colonies are restreaked twice on YPD before storing them as glycerol stock cultures at –70° C.

To exclude the presence of soraphen A resistant routants at the beginning of the cultivation of culture A, the remainder of culture A is plated on YPD-SOR-10 and incubated at 30° C. for 3 days. No growth of colonies is observed.

52 independent mutants are isolated using this protocol. 8 mutants of each mating type (YCI101, YCI103, YCI105, YCI115, YCI119, YCI126, YCI138, and YCI141 derived from YHV 18 and YCI1, YCI2, YCI10, YCI16, YCI37, YCI39, YCI43, and YCL51 derived from YS 18) which show rigorous growth are selected for further analysis.

In a first step all of the mutants are backcrossed with the wild-type strain of the opposite mating type, the diploid strains are sporulated and the asci are subjected to tetrad analysis. From each cross at least six complete tetra are examined and all of them are found to segregate 2:2 for soraphen A resistance and soraphen A sensitivity. This indicates mutations at a single genetic locus.

In another step the MIC of the dipbids from the backcrosses is determined. None of the diploids is as sensitive to soraphen A as the wild-type strain. Instead, a variety of semidominant or dominant phenotypes is found with a MIC ranging from 0,35 µg/ml to 54 µg/ml.

Finally 8 mutants of one mating type are crossed against one mutant of the other mating type. After sporulation and tetrad analysis all 4 spores of each tetrad are soraphen A resistant. No gene conversion is observed as expected with low numbers of tetrads. At least six complete tetrads from each cross are checked. The results indicate that all mutations map to the same genetic locus.

Example 4

Growth curves 100 ml YPD medium in a 500 ml flask is inoculated with about $10^7$ YS 18 yeast cells/ml and incubated for growth at 180 rpm at 30° C. Before the addition of soraphen A at time point 0, the cells have already been incubated for 1 hour. The control is treated identically, but receives no soraphen A. Total cell numers are monitored by measuring the OD600. The number of viable cells called the liter is determined by plating on YPD plates. The number of soraphen A resistant cells is counted by plating on YPD-SOR plates containing the same soraphen A concentration as in the flask.

In the presence of soraphen A a complete inhibition of growth is observed for approximately 40 hours; thereafter growth recovers due to soraphen A resistant mutants. The viable cell counts reveal that during the first 20 hours extensive cell killing occurs. The minimal inhibitory concentration (MIC) as determined from the growth curves is 0,1 µg/ml.

Example 5

Determination of the minimal inhibitory concentration (MIC)

Yeast colonies are grown for 2 days at 30° C. on a YPD plate and replica pated on a set of YPD-SOR plates. The following soraphen A concentrations are used: 0 µg/ml, 0,35 µg/ml, 0,76 µg/ml, 1,5 µg/ml, 3,13 µg/ml 6,7 µg/ml, 15,45 µg/ml and 54,5 µg/ml. After growth for 24 hours at 30° C. the plates are inspected for growth. Using this method the MIC for diploids from the backcrosses of soraphen A resistant yeast strains are determined to range from 0,35 µg/ml to 54 µg/ml.

Example 6

Cloning techniques

Restriction enzyme digestions and ligation reactions are performed as described in Maniatis et al, 'Molecular Cloning: A Laboratory Manual', Cold Spring Harbor Laboratory Press, 1989. Dephosphorylated cloning vector is prepared in the following way: 10 µl vector DNA (about 1 µg/µl), 2 µl restriction enzyme, 2 µl 10× restriction buffer and 6 gl of water are incubated at 37° C. for 2 hours. Then an additional 2 µl of restriction enzyme is added, and the sample incubated at 37° C. for 2 more hours. 3 µl bovine alkaline phosphatase (150 units/µl, Gibco BRL, Maryland, USA), 3 µl 10× dephosphorylation buffer (0,5M Tris-HCl pH 8, 0,5M NaCl) and 2 µl water are added and the tubes incubated for 1 hour at 65° C. The linearized and dephosphorylated vector is purified on a 0,7% TAE agarose gel. The DNA is then isolated from the gel slice using the gene clean kit (BIO101, California, USA). E.coli is transformed by electroporation (Dower et al, Nucleic Acid Res. 16:6127–6145) and plasmid DNA from E. coli is isolated using the Qiagen Midiprep Kit (Qiagen Inc., California, USA) or the Magic Miniprep Kit (Promega, Wis., USA).

Example 7

Preparation and screening of a gene bank for acetyl-CoA carboxylase in E. coli 40 µg chromosomal DNA of the mutant strain is digested with 50 units of SacI for 1 hour at 37° C. After 1 hour another 50 units of restriction enzyme are added and the incubation is continued for another hour. The digested DNA is electrophoresed on an 0,8% TAE gel, and fragments of 7,5 kb to 9 kb are isolated. The DNA fragments are cloned into the dephophorylated SacI site of pBlueKS+ (Stratagene) and transformed into E. coli. The resulting transformants are screened by colony hybridization probing with DNA comprising the known acetyl-CoA carboxylase wild-type gene.

Example 8

Colony hybridization

A DIG-labeled SacI restriction fragment containing the whole acetyl-CoA carboxylase coding region is prepared with the DIG Labeling Kit (Böhringer Mannhelm) according to the protocols of the manufacturer. Colonies are replica plated onto commercially available nylon filters allowing 5 minutes of contact. The filters are then placed onto Whatman 3M filter paper and soaked with the following solutions one after the other: 0,5M NaOH (5 min); 1M Tris-HCl pH 7,5 (2×1 min); 0,5M Tris-HCl pH 7,5 (1 min); and 1,5M NaCl (5 min). After air drying the filters are crosslinked for 3 minutes with UV light of 254 nm. Hybridization of filters and detection of positive colonies is performed using the DIG Luminescence Detection Kit (Böhringer Mannheim). The most stringent wash of the filters is performed in 0,1% SDS and 0,1× SSC at 58° C.

After screening of the gene banks prepared as described in example 7 seven clones were obtained: pCI2 (YCI2), pCI10 (YCI10), pCI39 (YCI39), pCI43 (YCI43), pCI101 (YCI101), pCI138 (YCI138), pCI141 (YCI141)

Example 9

Preparation and screening of a gene bank for acetyl-CoA carboxylase in yeast 40 µg genomic DNA of the mutant strain is digested with 0,8 units BamHI for 25 minutes (experimentally determined) at 37° C. The partially digested DNA is electrophoresed on an 0,8% agarose gel, and fragments of 6 kb to 10 kb are isolated. The DNA fragments are cloned into BamHI-cut and dephophorylated pRS316 (CEN6, ARSH4, URA3, Amp$^r$, ori; Sikorski et al, Genetics 122:19–27, 1989) and transformed into E. coli. The resulting transformants are dertransformatns are derided into 10 pools each containing clone pool is propagated once in 100 ml of LB medium containing 100 µg/ml ampicillin and plasmid DNA is prepared. The gene bank is screened by transforming yeast YS 18 with a fixed amount of DNA from each pool. The resulting SDHLS plates are replica plated twice on YPD-SOR-10. In order to avoid the selection of secondary soraphen A mutations, only the colonies that show resistance on both soraphen A containing plates are isolated from the SDHLS plates.

Using this method the acetyl-CoA carboxylase gene of the mutant YCI37 strain is isolated. The gene is able to restore soraphen A resistance to wild-type strains upon transformation.

Example 10

Yeast transformation using electroporation 5 ml of an overnight culture are diluted in 95 ml of YPD and grown for about 3 hours on a shaker with 180 rpm at 30° C. All the following steps are done at 4° C. or on ice. The culture is divided into two tubes and centrifuged for 5 minutes at 3000 rpm. The cells are washed 3 times in 50 ml of sterile water and once in 20 ml of 1M sorbitol. Finally the cells are resuspended in 200 µl of sterile 1M sorbitol and transformed in a 0,4 cm gap cuvette at 2,5 kV, 200 Ohm and 25 µF after mixing 40 µl of cells with up to 5 µg of DNA in up to 5 µl of sterile water. After the pulse the cells are immediately diluted with 1 ml 1M ice cold sorbitol. 100 µl to 1 ml of the cells are plated on SDHLS agar and incubated at 30° C. for 2–3 days.

Example 12

Restriction fragment shuffling

Several restriction fragments are shuffled between the wild-type acetyl-CoA carboxylase gene pCI18 obtained from YS 18 and the mutant gene pCI101. Resulting constructs are transformed into YS 18 and checked for their ability to confer soraphen A resistance. Based on the data, the mutation of pCI101 is mapped to the 1,9 kb SacI/NheI fragment comprising the N-terminal part of acetyl-CoA carboxylase and its promoter.

Example 13

DNA sequencing

DNA is sequenced using the dideoxy chain-termination method of Sanger et al, Procl. Natl. Acad. Sci. USA 74:5463–5467, 1977, using double-stranded plasmid DNA as a template. The oligonucleotide piers are synthesized on an Applied Biosystems Model 380 A Synthesizer.

The complete DNA sequence of the 1,9 kb DNA fragment shown in example 11 to be responsible for soraphen A resistance conferred by pCI101 is sequenced. It is found that a single base change results in the substitution of serine by a tyrosine residue at amino acid position 77. The same mutation is found for the acetyl-CoA carboxylase gene of the mutant YCI37 yeast strain. pCI141 also comprises this mutation but in addition contains mutations changing valine at amino acid position 50 to phenylalanine and histidine at amino acid position 53 to arginine. The mutations found in pCI43 change valine at amino acid position 50 to phenylalanine and lysine at amino acid position 73 to arginine. For pCI39 mutations have been found to change histidine at amino acid position 53 to arginine and threonine at amino acid position 57 to alanine.

Example 14

Purification of acetyl-CoA carboxylase acetyl-CoA carboxylase is enriched from 15 l of cells grown overnight in YPD medium at 30° C. using avidin-affinity chromatography. Cells are harvested by centrifugation and suspended in isolation buffer (200 mM potassium phosphate buffer pH 6,5; 5 mM β-mercaptoethanol; 1 mM EDTA; 100 g/l glycerol; 200 µM PMSF; 1 µM leupeptin; 1 µM pepstatin A; 0,66 µM antipain; 0,5 µM trypsin inhibitor (soybean); 200 µM TPCK; 100 µM TLCK) to give a final volume of 300 ml. Then 520 ml glassbeads (0,25–0,5 mm diameter) are added and the cells are homogenized in a bead mill for 5 minutes. Cell debris is removed by centirfugation, and the supernatant is filtered through glass wool preceding ultracentrifugation at 100 000 g at 4° C. After ultracentrifugation the supernatant is again filtered through glasswool and then 243 g/l ammoniumsulfate are added slowly to precipitate the proteins. Precipitated proteins are pelleted and resuspended in 24 ml column loading buffer (200 mM potassium phosphate buffer pH 6,5; 15 mM β-mercaptoethanol; 1 mM EDTA; 500 mM KCl; 3,1 mM Na$_3$N; 100 g/l glycerol; 200 µM PMSF; 1 µM leupeptin; 1 µM pepstatin A; 0,66 µM antipain; 0,5 µM trypsin inhibitor (soybean); 200 µM TPCK; 100 µM TLCK). The sample is applied on a C16 column (16 mm diameter) loaded with 10 ml monomeric avidin-agarose gel equilibrated with column loading buffer. The flow rate used is 1 ml/minute. Then the column is washed with column loading buffer until the OD$_{280}$ of the eluate is below 0,01. The fractions giving the highest extinctions at 280 nm are combined and protein is precipitated by slow addition of 243 g/l ammonium sulfate. The precipitated protein is pelleted, washed with ammonium sulfate-saturated loading buffer and then resuspended in 3 ml storage buffer (200 mM potassium phosphate buffer pH 6,5; 5 mM β-mercaptoethanol; 200 µ/l glycerol). Aliquoted enzyme solutions are stored at −70° C. Protein concentrations are determined according to Bradford (Bradford, Anal. Biochem 72:248–254, 1976).

Example 15

Enzymatic assay of acetyl-CoA carboxylase

Assays of enzymatic activity in the enriched fractions of wild-type and mutant strains can be performed in two different ways:

15.1. Incorporation of radioactively labeled hydrogencarbonate

In one method incorporated HCO$_3^-$ is distinguished from unincorporated HCO$_3^-$ by the different stability of HCO$_3^-$ and malonyl-coenzyme A in acidic solutions. HCO$_3$ is acid labile and is removed by heating the samples to 60° C. in a continous flow of nitrogen. Remaining radioactivity is present as malonyl-coenzyme A and is quantified to determine acetyl-CoA activity.

For the assay the following components are combined in a glass tube: 50 mM Tris-HCl pH 8, 10 mM MgCl, 7,5 g/l BSA (fatty acid free), 3,75 nM ATP, 10 mM EDTA, 10 µl (wild-type) or 25 µl (mutant) enzyme solution and different concentrations of soraphen A (0 µg/ml, 150 µg/ml, 1,5 µg/ml, 0,015 µg/ml). $^{14}$C-labeled NaHCO$_3$ is added at a concentration of 10 µCi per sample with specific activities of 52,4 µCi/µmol. The samples are brought to 200 µl with water, preincubated for 3 minutes at 30° C., and the reaction is started by addition of 0,5 mM acetyl-CoA. After 8 minutes the reaction is stopped by addition of 50 µl 5N HCl. 200 µl of the sample are dried at 60° C. under nitrogen and dissolved in 300 µl water. 5 ml of scintillation solution is added and the remaining radioactivity is measured in a scintillation counter. As a control for unspecific incorporation Of H$^{14}$CO$_3^-$ the reaction is performed without addition of acetyl-CoA. The results are then corrected for unspecific incorporation.

15.2. Spectrophotometric assay for acetyl-CoA carboxylase activity

In this method the byproduct of the acetyl-CoA carboxylase reaction ADP is measured: ADP and phosphoenolpyruvate are converted to pyruvate by pyruvate kinase which is then reduced to lactate by lactatedehydrogenase under oxidation of NADH. The oxidation rate of NADH can be quantitatively measured at 340 nm (Matsuhashi in: 'Methods of enzymology', 14:3–6).

The assay is performed in plastic cuvettes using the following reaction mixture: 50 mM Tris-HCl pH 8; 10 mM MgCl; 10 mM EDTA, 0,25 mM NADH; 3,75 nM ATP; 25 mM KHCO$_3$; 1,0 mM phosphoenolpyruvate; 0,6 mg BSA; 4 units pyruvate kinase; 4,5 units lactate dehydrogenase; 60 µl enzyme solution and optionally different concentrations of soraphen A (0 µg./ml, 150 µg/ml, 1,5 µg/ml, 0,015 µg/ml). Water is added to give a final volume of 0,8 ml. The reaction is started by addition of 0,1 µM acetyl-CoA. The OD$_{340}$ is monitored for the first 5 minutes after start of the reaction. When this assay is used it has to be considered that copurified pyruvatecarboxylase will disturb the assay and give a background of 15%.

---

What is claimed is:

1. An isolated and purified DNA molecule from yeast encoding an acetyl-coenzyme A carboxylase having a mutation conferring resistance to Soraphen A, wherein said mutation is a substitution of a tyrosine residue for a serine residue, wherein said serine residue is located at amino acid position 77 of SEQ ID NO:1.

2. A method of producing purified recombinant fungal acetylcoenzyme a carboxylase resistant to Soraphen A, comprising:

(a) transforming a host organism selected from the group consisting of bacteria, yeast and insert cells with a DNA molecule according to claim 1; and (b) isolating said acetyl-coenzyme A carboxylase from the host organism or its culture supernatant.

3. A method according to claim 2, wherein said host organism is yeast.

\* \* \* \* \*